United States Patent
Hamilton

(10) Patent No.: US 12,030,886 B2
(45) Date of Patent: Jul. 9, 2024

(54) FORM OF PONATINIB

(71) Applicant: MACFARLAN SMITH LIMITED, Edinburgh (GB)

(72) Inventor: Clifton R. Hamilton, Devens, MA (US)

(73) Assignee: MACFARLAN SMITH LIMITED, Edinburgh (GB)

( * ) Notice: Subject to any disclaimer, the term of this patent is extended or adjusted under 35 U.S.C. 154(b) by 769 days.

(21) Appl. No.: 17/247,471

(22) Filed: Dec. 11, 2020

(65) Prior Publication Data

US 2021/0094961 A1    Apr. 1, 2021

Related U.S. Application Data

(63) Continuation of application No. PCT/US2019/038396, filed on Jun. 21, 2019.

(60) Provisional application No. 62/688,788, filed on Jun. 22, 2018.

(51) Int. Cl.
*C07D 487/04*    (2006.01)

(52) U.S. Cl.
CPC ........ *C07D 487/04* (2013.01); *C07B 2200/13* (2013.01)

(58) Field of Classification Search
CPC .... C07D 487/04; A61P 35/00; C07B 2200/13
See application file for complete search history.

(56) References Cited

U.S. PATENT DOCUMENTS

| | | | |
|---|---|---|---|
| 8,114,874 B2 | 2/2012 | Zou et al. | |
| 9,029,533 B2 | 5/2015 | Zou et al. | |
| 9,456,992 B2 | 10/2016 | Brisander et al. | |
| 9,493,470 B2 | 11/2016 | Murray et al. | |
| 9,493,473 B2 | 11/2016 | Kovi et al. | |
| 9,725,454 B2 | 8/2017 | Stefinovic et al. | |
| 10,221,184 B2 | 3/2019 | Kovi et al. | |
| 2013/0178622 A1 | 7/2013 | Huang et al. | |
| 2016/0362411 A1 | 12/2016 | Kovi et al. | |
| 2016/0368917 A1 | 12/2016 | Zou et al. | |
| 2017/0190707 A1 | 7/2017 | Murray et al. | |
| 2018/0044345 A1 | 2/2018 | Kovi et al. | |
| 2019/0031656 A1 | 1/2019 | Zou et al. | |

FOREIGN PATENT DOCUMENTS

| | | |
|---|---|---|
| CN | 105646494 A * | 6/2016 |
| WO | 2014093579 A2 | 6/2014 |
| WO | 2015085972 A1 | 6/2015 |
| WO | 2015085973 A1 | 6/2015 |
| WO | 2017200826 A1 | 11/2017 |
| WO | 2018232501 A1 | 12/2018 |

OTHER PUBLICATIONS

English translation of CN 105646494 A, publ. Jun. 8, 2016 (Year: 2016).*

Caira, Mino R., "Crystalline Polymorphism of Organic compounds", Topics in Current Chemistry, Jan. 1998 (vol. 198) pp. 163-208.

* cited by examiner

*Primary Examiner* — Sarah Pihonak

(57) ABSTRACT

The present disclosure relates to Form Z of acetic acid solvated hydrate of ponatinib hydrochloride. The present disclosure is also related to processes for the preparation of Form Z of acetic acid solvated hydrate of ponatinib hydrochloride. Further, the present disclosure also relates to pharmaceutical compositions comprising Form Z of acetic acid solvated hydrate of ponatinib hydrochloride and methods for treating disease using Form Z of acetic acid solvated hydrate of ponatinib hydrochloride.

16 Claims, 6 Drawing Sheets

FORM OF PONATINIB

CROSS-REFERENCE TO RELATED APPLICATIONS

This application is a continuation of international application No. PCT/US2019/038396, filed Jun. 21, 2019, which claims priority to U.S. Provisional Patent Application No. 62/688,788, filed Jun. 22, 2018, the disclosures of which are incorporated herein by reference in their entireties for all purposes.

FIELD OF THE DISCLOSURE

The present disclosure relates to Form Z of acetic acid solvated hydrate of ponatinib hydrochloride. The present disclosure is also related to processes for the preparation of Form Z of acetic acid solvated hydrate of ponatinib hydrochloride. Further, the present disclosure also relates to pharmaceutical compositions comprising Form Z, and methods for treating disease using Form Z of acetic acid solvated hydrate of ponatinib hydrochloride.

BACKGROUND OF THE DISCLOSURE

Ponatinib, having the chemical designation 3-(imidazo[1,2-b]pyridazin-3-ylethynyl)-4-methyl-N-{4-[(4-methylpiperazin-1-yl)methyl]-3-(trifluoromethyl)phenyl}benzamide, is an orally bioavailable multi-targeted tyrosine-kinase inhibitor. Ponatinib has the following structure:

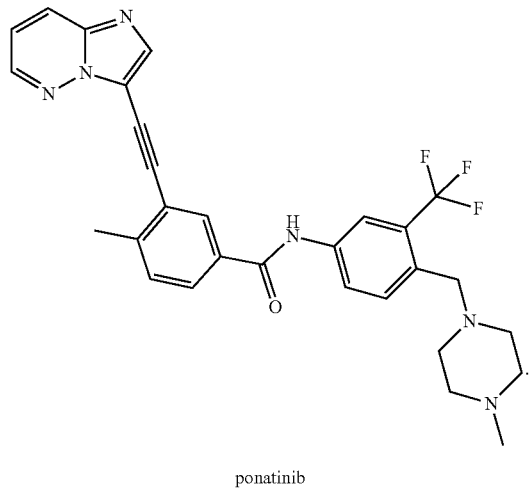 [SMILES: Cc1ccc(C(=O)Nc2ccc(CN3CCN(C)CC3)c(C(F)(F)F)c2)cc1C#Cc1cnc2cccnn12]

ponatinib

Ponatinib is commercially marketed under the name Iclusig® and is indicated for the treatment of chronic phase, accelerated phase, or blast phase chronic myeloid leukemia (CIVIL) or Philadelphia chromosome positive acute lymphoblastic leukemia (Ph+ ALL) in adult patients who are resistant or intolerant to other tyrosine kinase inhibitor therapy.

Ponatinib is described in U.S. Pat. Nos. 8,114,874, 9,456,992 and U.S. Publication No. 20160368917. Solid forms of ponatinib are described in U.S. Pat. No. 9,493,470 (Form A) and U.S. Pat. No. 9,725,454 (Forms 1 and 8), U.S. Publication Nos. 20170190707 (Forms B-K) and International Publication No. WO2015085973 (Forms 1-10). Salts of ponatinib are described in U.S. Publication No. 20180044345 (hydrobromic acid) and International Publication No. WO2015085972 (benzoic acid, citric acid, fumaric acid, L-tartaric acid, maleic acid, phosphoric acid, sulphuric acid, succinic acid and p-toluenesulphonic acid). Methods of treating CML or Ph+ ALL using ponatinib are described in U.S. Pat. No. 9,029,533. Methods of treating cancer using ponatinib are described in International Publication No. WO2017200826. Processes for preparing forms of ponatinib are described in U.S. Pat. No. 9,493,473 and U.S. Patent Publication Nos. 20130178622 and 20160362411. None of the references describe Form Z of acetic acid solvated hydrate of ponatinib hydrochloride.

SUMMARY OF THE DISCLOSURE

The present disclosure relates to Form Z of acetic acid solvated hydrate of ponatinib hydrochloride. The present disclosure is also related to processes for the preparation of Form Z of acetic acid solvated hydrate of ponatinib hydrochloride. Further, the present disclosure also relates to pharmaceutical compositions comprising Form Z of acetic acid solvated hydrate of ponatinib hydrochloride and methods for treating disease using Form Z of acetic acid solvated hydrate of ponatinib hydrochloride.

DETAILED DESCRIPTION OF THE DISCLOSURE

Figure 1:
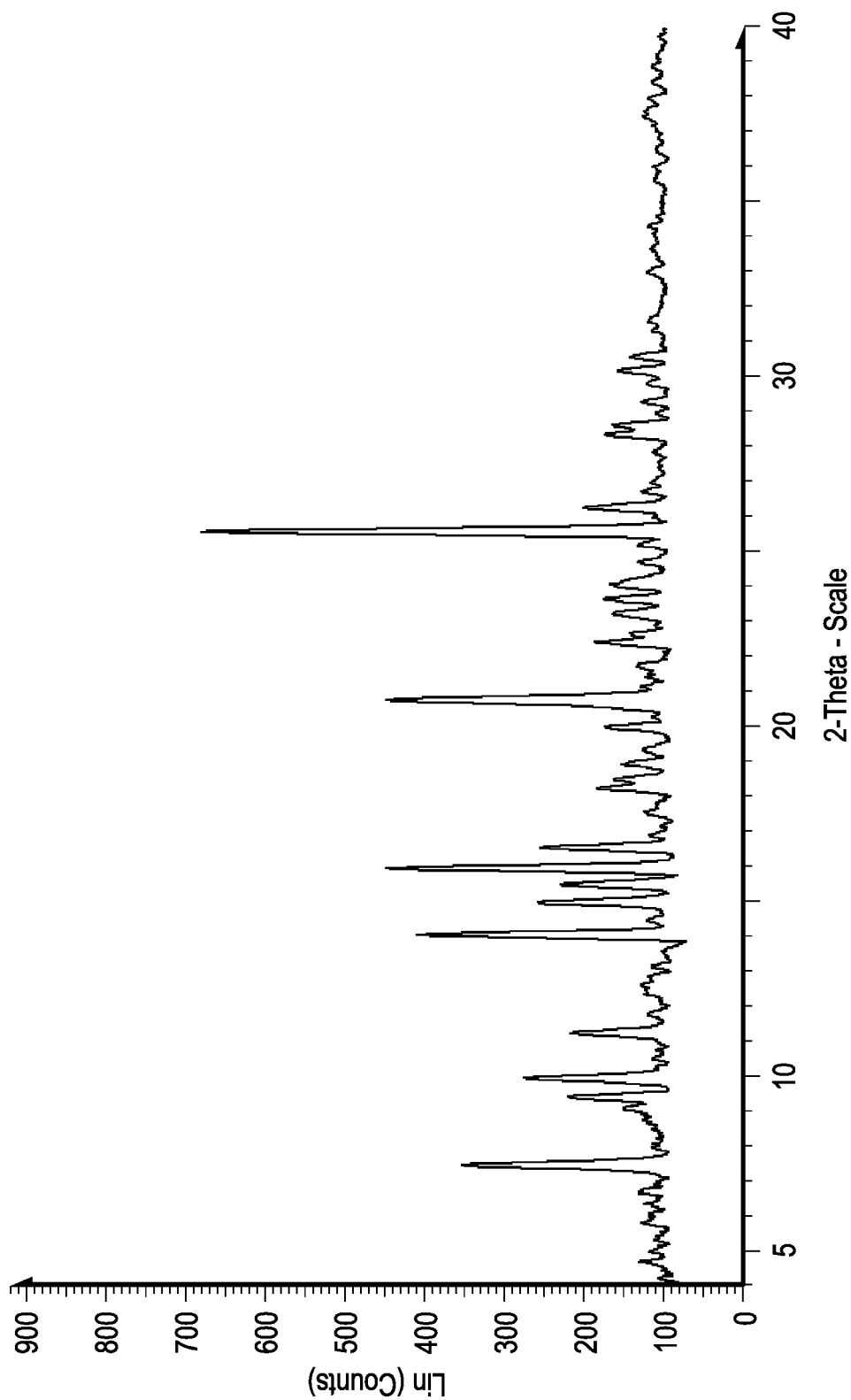
FIG. 1 is a representative XRPD pattern of Form Z of acetic acid solvated hydrate of ponatinib hydrochloride.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are not intended to be limited to the examples described herein and shown, but are to be accorded the scope consistent with the claims.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form.

As used herein and unless otherwise specified, the term "pharmaceutical composition" is intended to encompass a pharmaceutically effective amount of the ponatinib of the invention and a pharmaceutically acceptable excipient. As used herein, the term "pharmaceutical compositions" includes pharmaceutical compositions such as tablets, pills, powders, liquids, suspensions, emulsions, granules, capsules, suppositories, or injection preparations.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "excipient" refers to a pharmaceutically acceptable organic or inorganic carrier substance. Excipients may be natural or synthetic substances formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

As used herein and unless otherwise specified, the term "patient" refers to an animal, preferably a mammal, most preferably a human, who has been the object of treatment, observation or experiment. Preferably, the patient has experienced and/or exhibited at least one symptom of the disease or disorder to be treated and/or prevented. Further, a patient may not have exhibited any symptoms of the disorder, disease or condition to be treated and/prevented, but has been deemed by a physician, clinician or other medical professional to be at risk for developing said disorder, disease or condition.

As used herein and unless otherwise specified, the terms "polymorph," "polymorphic form" or related term herein, refer to a crystal form of one or more molecules, or solvate or salt thereof that can exist in two or more forms, as a result different arrangements or conformations of the molecule(s), or solvate molecule or salt ion thereof in the crystal lattice of the polymorph.

As used herein and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more therapeutic agents to a patient with such a disease or disorder. In some embodiments, the terms refer to the administration of a compound provided herein, with or without other additional active agents, after the onset of symptoms of a disease.

It is therefore an object of the present disclosure to provide Form Z acetic acid solvated hydrate of ponatinib hydrochloride that is purifiable, stable and scalable. It is also the object of the present disclosure to provide Form Z acetic acid solvated hydrate of ponatinib hydrochloride that is capable of being isolated and handled. It is further an object of the present disclosure to provide a process for the preparation of such Form Z acetic acid solvated hydrate of ponatinib hydrochloride. It is yet another object of the disclosure to use Form Z acetic acid solvated hydrate of ponatinib hydrochloride to prepare a pharmaceutical dosage form of ponatinib.

In one embodiment, the Form Z acetic acid solvated hydrate of ponatinib hydrochloride may contain about 0.75 moles to about 1.25 moles of water per mole of ponatinib.

In another embodiment, the Form Z acetic acid solvated hydrate of ponatinib hydrochloride is a monohydrate.

In one embodiment, ponatinib freebase is dissolved in a mixture of acetic acid and ethyl acetate to form a solution and stirred. Aqueous hydrochloride is dissolved in isopropyl alcohol. The aqueous hydrochloride/isopropyl alcohol mixture is added to the ponatinib solution at about 50° C. The solution is stirred at about 0° C. and the resulting precipitate is filtered and dried.

In another embodiment, ponatinib freebase is dissolved in a mixture of acetic acid, methanol and ethyl acetate to form a solution. The solution is stirred at about 50° C. and hydrochloride in 2-pentanol is added with ethyl acetate. The volume is reduced at about 88° C. The material crystallizes at about −5° C. for several hours. The resulting precipitate is filtered and dried.

In another embodiment, ponatinib freebase is dissolved in a mixture of acetic acid and ethyl acetate. The solution is stirred and a dilute mixture of hydrochloride in isopropyl alcohol is dripped into the ponatinib solution while stirring at about 50° C. The solution is cooled to about −5° C. and stirred overnight. The resulting precipitate is filtered and dried.

In yet another embodiment, the ratio of ponatinib freebase to hydrochloride is an about a 1:1 molar ratio.

In yet another embodiment, the hydrochloride is mixed with any organic solvent.

The organic solvent may be heptane, ethyl acetate or isopropyl alcohol.

In yet another embodiment, optionally, the filtered product may be rinsed before drying with a solvent which gives low or poor solubility for ionic or highly polar species. The solvent may be a solvent such as heptane, ethyl acetate, isopropyl alcohol, toluene or 2-pentanol.

In yet another embodiment, the filtered product may be air dried at a temperature up to about 60° C.

In yet another embodiment, the filtered product may be dried under vacuum for up to about 8 hours at about 45° C.

In yet another embodiment, the filtered product may be dried under vacuum up to about 2 days at about 30° C.

The present disclosure provides for a method of treating disease by administering to a patient, in need thereof, a pharmaceutical composition comprising Form Z of acetic acid solvated hydrate of ponatinib hydrochloride according to the disclosure. Ponatinib is indicated for the treatment of chronic phase, accelerated phase, or blast phase chronic myeloid leukemia (CIVIL) or Philadelphia chromosome positive acute lymphoblastic leukemia (Ph+ ALL) in adult patients who are resistant or intolerant to other tyrosine kinase inhibitor therapy.

The present disclosure also encompasses pharmaceutical compositions comprising the Form Z of acetic acid solvated hydrate of ponatinib hydrochloride according to the disclosure. Pharmaceutical compositions containing the Form Z of acetic acid solvated hydrate of ponatinib hydrochloride according to the disclosure may be prepared according to U.S. Pat. No. 8,114,874, which is incorporated herein by reference in its entirety. The dosage of the pharmaceutical compositions may be varied over a wide range. Optimal dosages and dosage regimens to be administered may be readily determined by those skilled in the art, and will vary with the mode of administration, the strength of the preparation and the advancement of the disease condition. In addition, factors associated with the patient being treated, including patient's sex, age, weight, diet, physical activity, time of administration and concomitant diseases, will result in the need to adjust dosages and/or regimens. In the use of Form Z of acetic acid solvated hydrate of ponatinib hydrochloride as the active agent, the recommended dose of ponatinib therein is 45 mg, orally, once daily or 30 mg, orally, once daily for patients with hepatic impairment. For example, a dosage of ponatinib in Form Z of acetic acid solvated hydrate of ponatinib hydrochloride in the pharmaceutical composition of the disclosure is available as tablets in amounts of 15 mg, 30 mg, or 45 mg.

EXAMPLES

Examples, which follow herein, are directed to embodiments of the invention. The examples are presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles described herein may be applied to other examples and applications without departing from the spirit and scope of the various embodiments. Therefore, the various embodiments are illustrative of the present disclosure and the disclosure is not intended to be limited to the examples described herein and shown.

Analytical Techniques

XRPD patterns are obtained using a Bruker D8 Advance equipped with a Cu Kα radiation source (λ=1.54 Å), a 9-position sample holder and a LYNXEYE super speed detector. Samples are placed on zero-background, silicon plate holders for analysis. One skilled in the art would recognize that the ° 2θ values and the relative intensity values are generated by performing a peak search on the measured data and the d-spacing values are calculated by the instrument from the ° 2θ values using Bragg's equation. One skilled in the art would further recognize that the relative intensity for the measured peaks may vary as a result of sample preparation, orientation and instrument used, for example.

DSC data are collected using a TA Instruments Q10 DSC. Approximately, samples (2-8 mg) are placed in unsealed but covered hermetic alodined aluminum sample pans and scanned from about 30 to about 350° C. at a rate of about 10° C./min under a nitrogen purge of about 50 mL/min.

Some of the DSC runs are generated using a TA Instruments Q2000 equipped with an auto-sampler and RSC40. The sampling is conducted at a ramp rate of about 10° C./min from 20° C. to 320° C. using hermetic sealed aluminum sample pans. For mDSC (modulated DSC) data, samples are equilibrated at 5° C. with a ramp rate of 1.5° C. to 320° C., modulated ±0.50° C. every 60 seconds.

TGA measurements are recorded using a TA Q500 instrument. The samples are weighed in aluminum pans. TGA investigations are performed at a heating rate of 10.0° C./min over a temperature range of from about 25 to about 300° C., with purging with nitrogen at a flow rate of 60 mL/min.

$^1$H NMR data are collected using a Bruker Avance 300 MHz NMR equipped with TopSpin software. Samples are prepared by dissolving the compound in deuterated dimethylsulfoxide with 0.05% (v/v) tetramethylsilane (TMS). Spectra are collected at ambient temperature. The number of scans was 16 for $^1$H-NMR.

Crystalline morphology of samples is analyzed using an Olympus BX53 polarized light microscope equipped with a PAXcam 3 digital microscope camera.

EXPERIMENTAL

Examples 1-3 below provide embodiments of the preparation of acetic acid solvated hydrate of ponatinib hydrochloride.

Example 1

Preparation of Form Z of Acetic Acid Solvated Hydrate of Ponatinib Hydrochloride About 1.7 g of ponatinib freebase is dissolved in a mixture of about 2 mL of acetic acid and about 3 mL of ethyl acetate to form a solution and stirred. About 272 μL of about 11.65 M aqueous hydrochloride is dissolved in about 10 mL of isopropyl alcohol. The aqueous hydrochloride/isopropyl alcohol mixture is added over about two minutes to the stirring ponatinib solution at about 50° C. The solution is stirred at about 0° C. for about 1.5 hours. The resulting precipitate is filtered, rinsed with isopropyl alcohol and dried under vacuum.

FIG. 1 is a representative XPRD pattern for Form Z of acetic acid solvated hydrate of ponatinib hydrochloride and 2θ, d-spacing and relative % intensity values for peaks are shown in Table I.

TABLE I

| Angle (2-Theta °) | Intensity (%) |
|---|---|
| 7.4 | 43.5 |
| 9.3 | 20.3 |
| 9.9 | 29.9 |
| 11.2 | 19.8 |
| 14.0 | 53.2 |
| 14.9 | 27 |
| 15.4 | 22 |
| 15.9 | 59.9 |
| 16.5 | 26.3 |
| 18.1 | 14.1 |
| 18.9 | 8.8 |
| 19.9 | 12.4 |
| 20.7 | 59.7 |
| 21.6 | 5.5 |
| 22.3 | 14.5 |
| 23.1 | 10.8 |
| 23.6 | 12.6 |
| 24.0 | 11.4 |
| 25.5 | 100 |
| 26.2 | 17.1 |
| 28.3 | 12.5 |
| 28.5 | 10.7 |
| 30.1 | 9.6 |
| 30.5 | 6.8 |

The angle measurements are ±0.2° 2θ. Key defining peaks for Form Z of acetic acid solvated hydrate of ponatinib hydrochloride include 7.4, 23.6, 25.5, 30.1 and 30.5° 2θ degrees.

Figure 2:
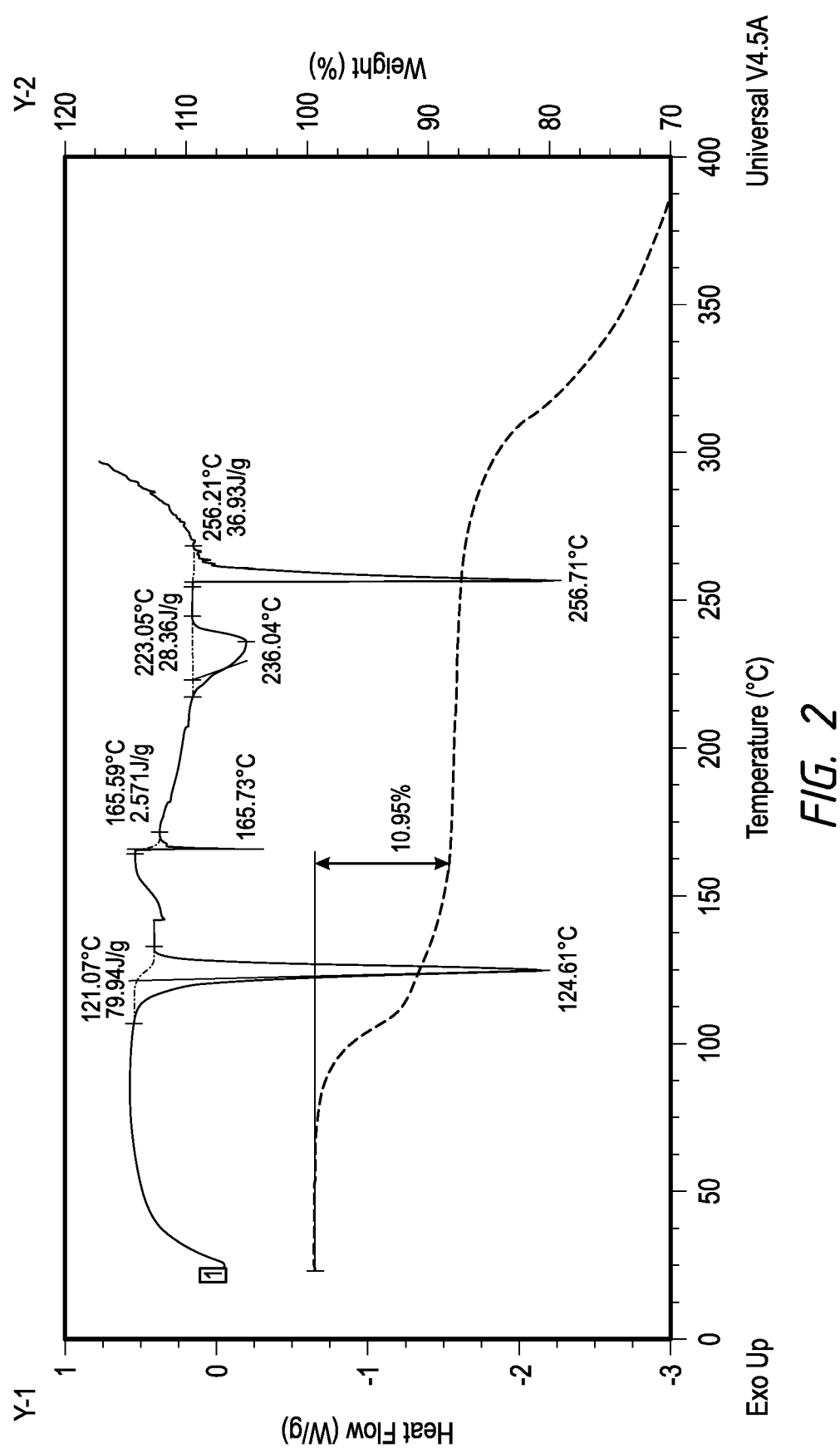
FIG. 2 are DSC and TGA plots of Form Z of acetic acid solvated hydrate of ponatinib hydrochloride.

The DSC and TGA plots (FIG. 2) show TGA weight loss of about 9.5-14% by about 200° C. and the DSC shows a thermal event at about 125° C. for Form Z of acetic acid solvated hydrate of ponatinib hydrochloride.

Figure 3:
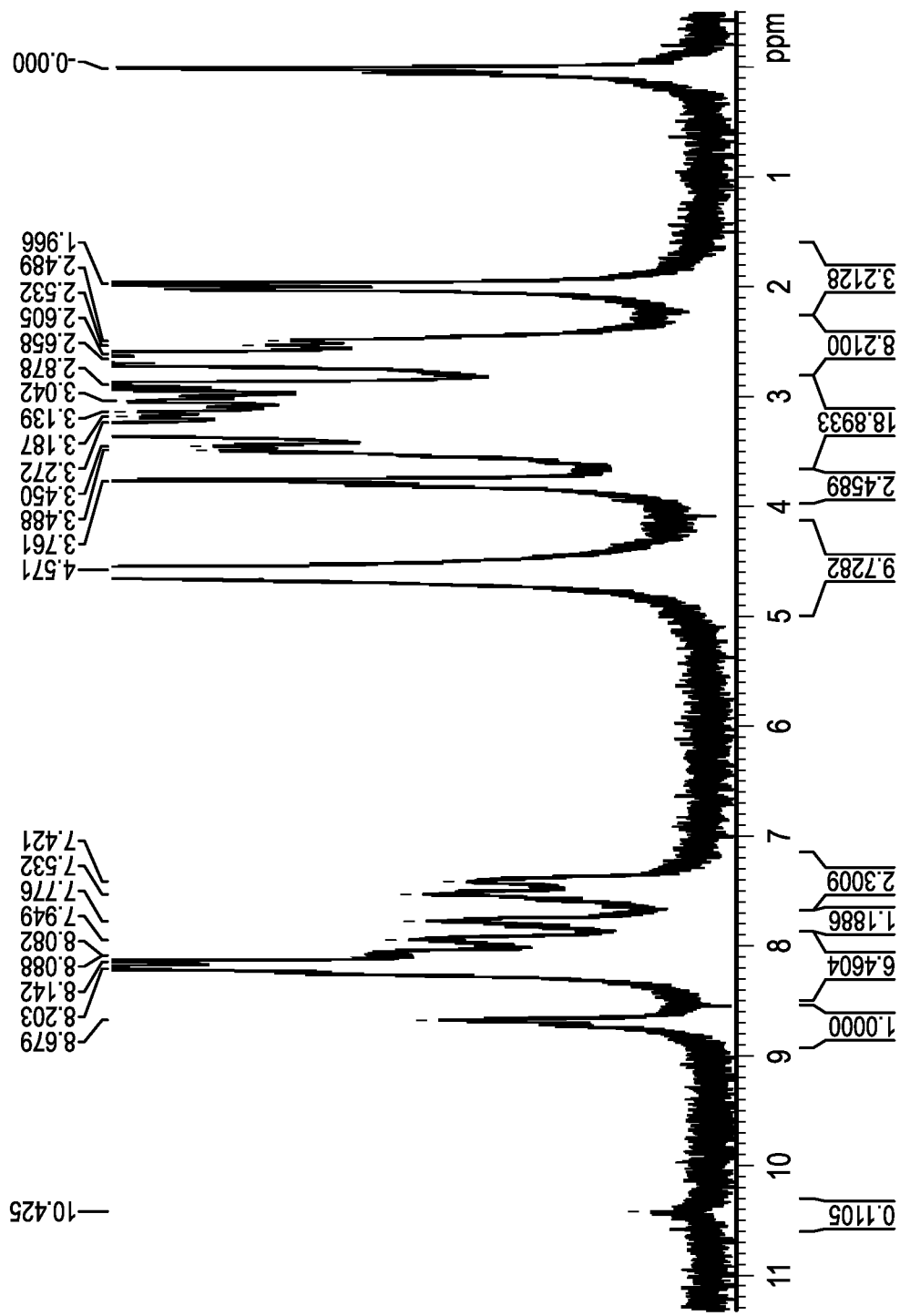
FIG. 3 is a $^1$H NMR spectra of Form Z of acetic acid solvated hydrate of ponatinib hydrochloride.

FIG. 3 is directed to the $^1$H NMR for the Form Z of acetic acid solvated hydrate of ponatinib hydrochloride.

Figure 4:
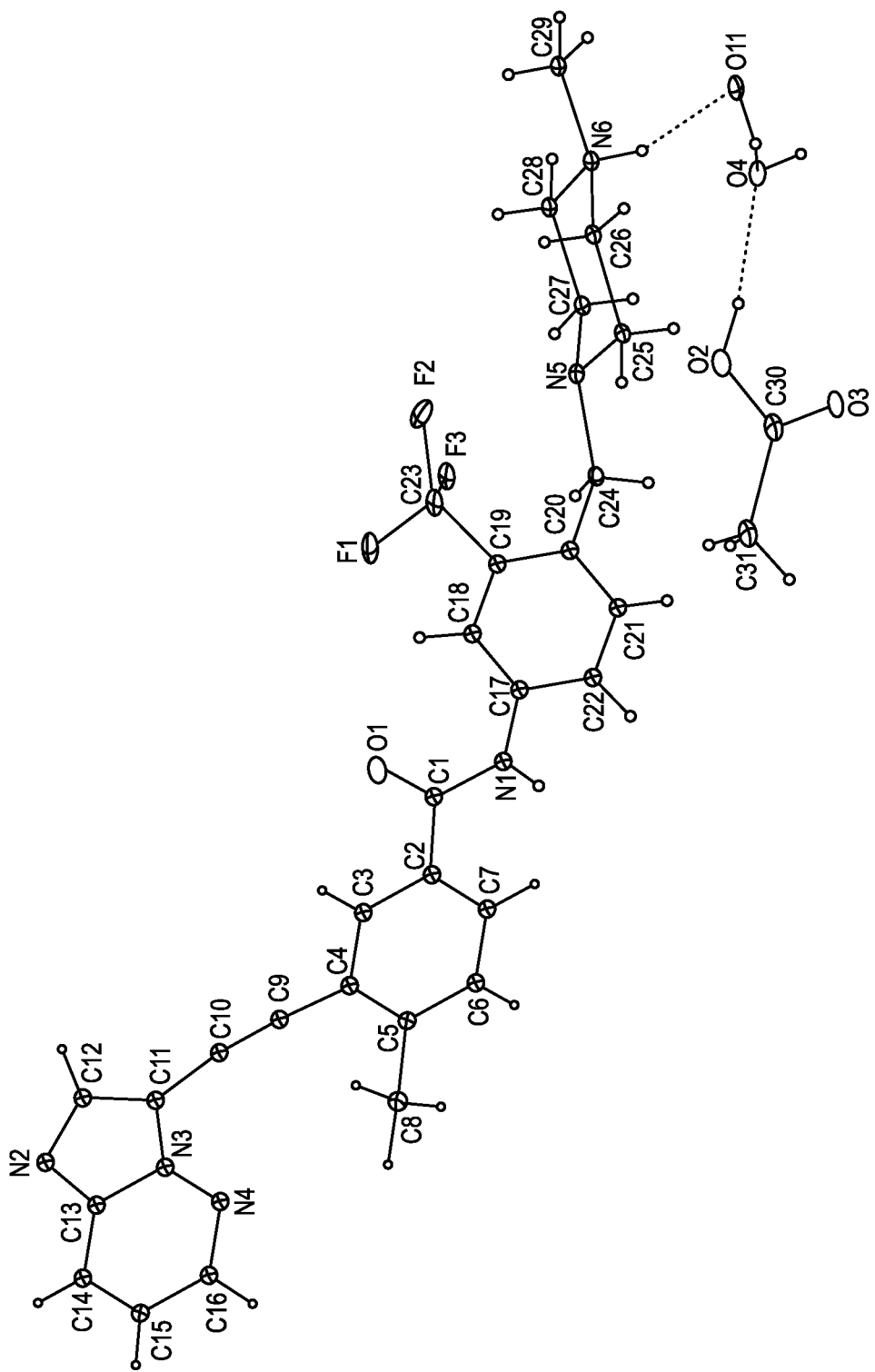
FIG. 4 is a three-dimensional structure of Form Z of acetic acid solvated hydrate of ponatinib hydrochloride.
Figure 5:
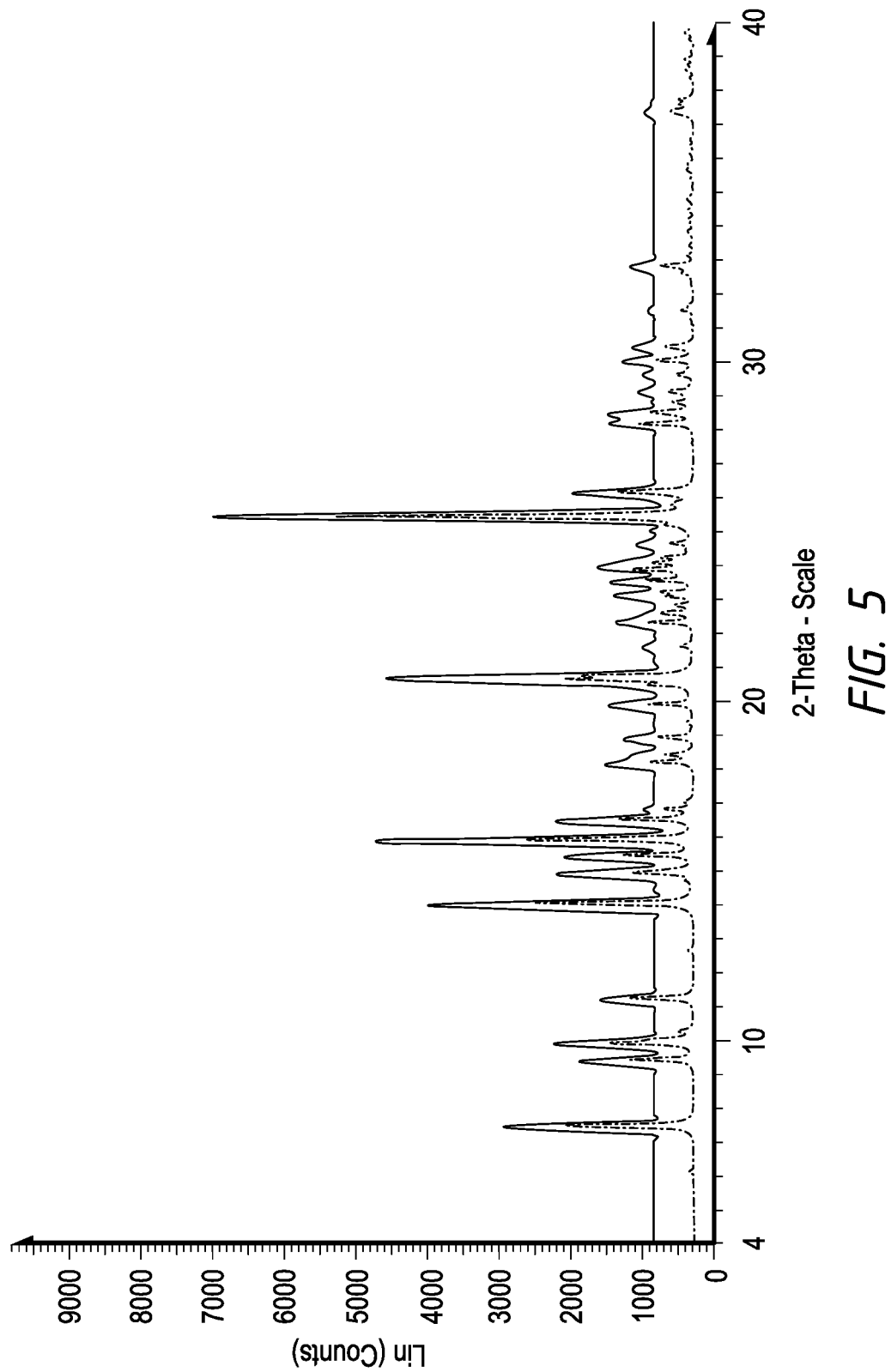
FIG. 5 shows the calculated XRPD pattern of Form Z of acetic acid solvated hydrate of ponatinib hydrochloride as determined by SCXRD (bottom) is in good agreement with the XRPD for Form Z of acetic acid solvated hydrate of ponatinib hydrochloride (top).

FIG. 4 shows the three-dimensional structure of Form Z of acetic acid solvated hydrate of ponatinib hydrochloride that is discerned from SCXRD. The single crystal parameters for Form Z of acetic acid solvated hydrate of ponatinib hydrochloride are:

a=9.2228 (15) Å;
b=12.283 (2) Å;
c=14.587 (2) Å;
α=84.923° (8°), β=82.932 (8°) γ=70.753 (8°);
Volume: 1546.3(5) Å$^3$; and
Z=2, Z'=1.

Figure 6:
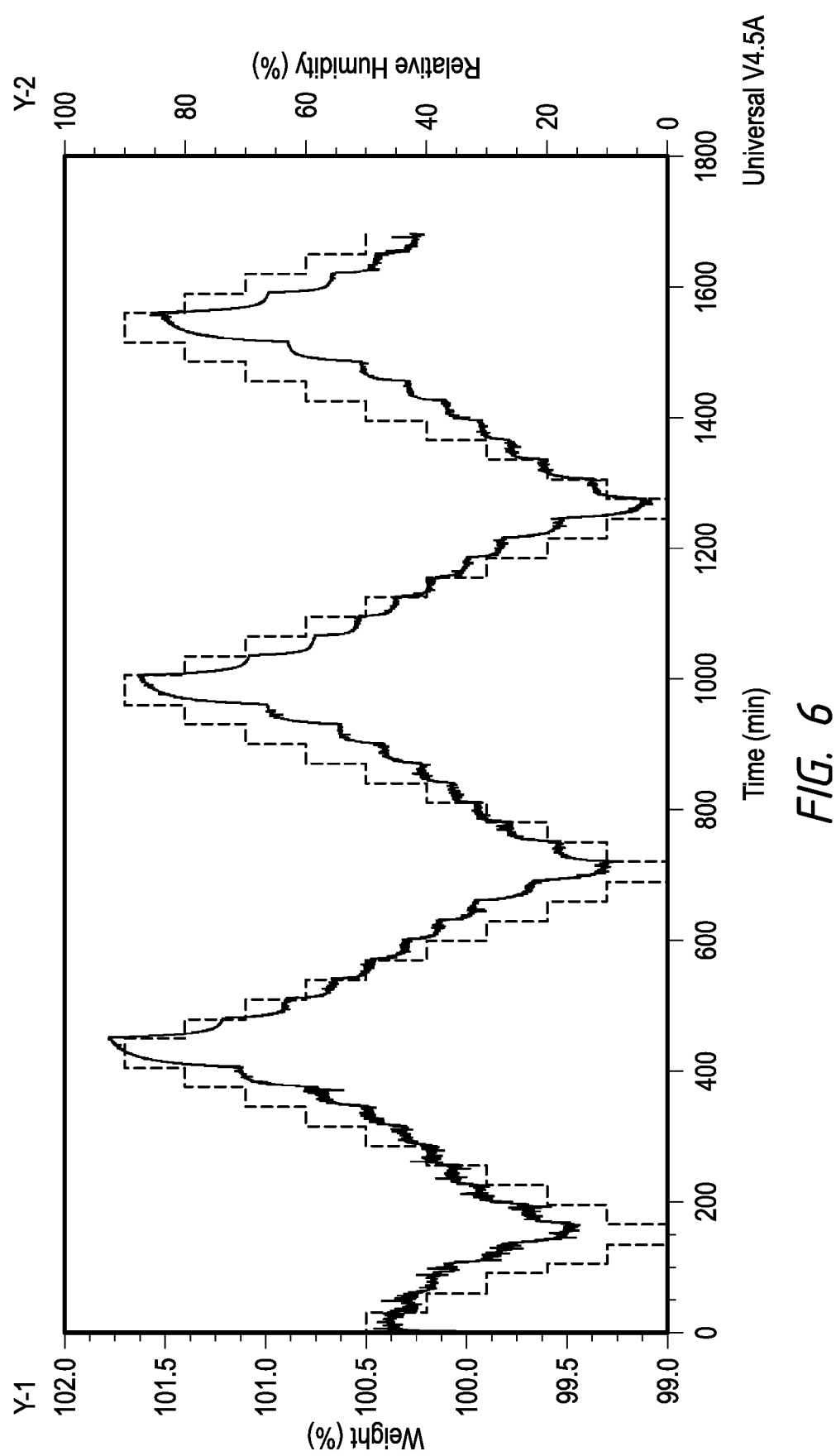
FIG. 6 is a DVS plot of Form Z of acetic acid solvated hydrate of ponatinib hydrochloride.

Form Z of acetic acid solvated hydrate of ponatinib hydrochloride is stable under stressed conditions of about 40° C./75% RH and about 25° C./97% RH for at least four weeks. FIG. 6 shows the DVS of the Form Z of acetic acid solvated hydrate of ponatinib hydrochloride.

Example 2

Preparation of Form Z of Acetic Acid Solvated Hydrate of Ponatinib Hydrochloride About 1 g of ponatinib freebase is dissolved in a mixture of about 2 mL of acetic acid, about 2 mL of methanol and about 8 mL of ethyl acetate to form a solution. The solution is stirred at about 50° C. for about 1 hour. About 300-374 μL of about 5-6 M hydrochloride in 2-pentanol is added with about 7 mL of ethyl acetate. The volume is reduced to about 16 mL at about 88° C. The material crystallizes at about −5° C. for about several hours and is filtered. The filtered product is rinsed with ethyl acetate and dried under vacuum.

Example 3

Preparation of Form Z of Acetic Acid Solvated Hydrate of Ponatinib Hydrochloride About 1 g of ponatinib freebase is dissolved in a mixture of about 1 mL of acetic acid and about 9 mL of ethyl acetate to form a solution. The solution is stirred and a dilute mixture of hydrochloride in isopropyl alcohol and ethyl acetate is dripped into the ponatinib solution while stirring at about 50° C. The solution is cooled to about −5° C. while stirring. The solution stirs overnight and is then vacuum filtered. The filtered product is rinsed with ethyl acetate, then dried under vacuum.

The above examples are presented to aid in the understanding of the disclosure and enable a person of ordinary skill in the art to make and use the various embodiments, and are not intended and should not be construed to limit in any way the disclosure set forth in the claims which follow hereafter.

What is claimed is:

1. A compound which is an acetic acid solvated hydrate of ponatinib hydrochloride.

2. The compound according to claim 1, wherein the compound is a monohydrate.

3. The compound according to claim 1, wherein the compound is characterized by having at least 2 or more X-ray powder diffraction peaks selected from about 7.4, 23.6, 25.5, 30.1 and 30.5° 2θ measured by CuKα radiation.

4. The compound according to claim 1, wherein the compound is characterized by a thermal event at about 125° C., as measured by differential scanning calorimetry.

5. The compound according to claim 1, characterized by a weight loss of about 9.5% to about 14% from about 100° C. through about 200° C., as measured by thermal gravimetric analysis.

6. The compound according to claim 1, wherein the compound is characterized by single crystal parameters of about a=9.2228 (15) Å;
b=12.283 (2) Å;
c=14.587 (2) Å;
α=84.923° (8°), β=82.932 (8°), γ=70.753 (8°).

7. The compound according to claim 1, wherein the cell volume is about 1546.3 Å3.

8. A pharmaceutical composition comprising a pharmaceutically effective amount of the compound according to claim 1 and pharmaceutically acceptable excipient.

9. A method of preparing the compound according to claim 1, comprising:
   a. dissolving ponatinib freebase in a mixture of acetic acid and ethyl acetate or a mixture of acetic acid, methanol and ethyl acetate to yield a solution;
   b. adding hydrochloride in an organic solvent to the solution; and
   c. cooling the solution to precipitate the acetic acid solvated hydrate of ponatinib hydrochloride.

10. The method of claim 9, wherein the molar ratio of ponatinib to hydrochloride is about 1:1.

11. The method of claim 9, wherein the organic solvent is isopropyl alcohol, ethyl acetate, 2-pentanol, or any mixture thereof.

12. The method of claim 9, wherein the precipitate is rinsed with a solvent selected from the group consisting of isopropyl alcohol, heptane, ethyl acetate, toluene or 2-pentanol.

13. The method of claim 12, wherein the solvent is isopropyl alcohol, heptane or ethyl acetate.

14. The method of claim 9, wherein step b is carried out at about 50° C.

15. The method of claim 9, wherein the cooling is to at least about 0° C.

16. A method of preparing the compound according to claim 1, comprising:
   a. dissolving ponatinib freebase in a mixture of acetic acid and ethyl acetate to yield a solution;
   b. adding aqueous hydrochloride dissolved in isopropyl alcohol to the solution; and
   c. cooling the solution to about 0° C. to yield a precipitate comprising the acetic acid solvated hydrate of ponatinib hydrochloride.

* * * * *